United States Patent [19]

Haut et al.

[11] 4,366,317

[45] Dec. 28, 1982

[54] PROCESS FOR SYNTHESIS OF N-(HYDROCARBYL)SUBSTITUTED-P-MENTHANE-3-CARBOXAMIDE

[75] Inventors: Stephen A. Haut, Chesterfield; Roger A. Comes, Midlothian, both of Va.

[73] Assignee: Philip Morris Incorporated, New York, N.Y.

[21] Appl. No.: 276,328

[22] Filed: Jun. 22, 1981

[51] Int. Cl.$^3$ .................. C07C 102/00; C07D 241/00; C07D 213/00

[52] U.S. Cl. .................. 544/336; 544/406; 546/309; 548/200; 549/70; 549/480; 564/44; 564/123

[58] Field of Search .................. 564/123, 44; 544/406, 544/336; 546/309; 548/200; 549/70; 260/347.3

[56] References Cited

U.S. PATENT DOCUMENTS

| | | | |
|---|---|---|---|
| 3,483,248 | 12/1969 | Pattison | 250/515 |
| 3,898,073 | 8/1975 | Fitzgerald et al. | 71/93 |
| 4,150,052 | 4/1979 | Watson et al. | 564/123 |
| 4,178,459 | 12/1979 | Watson et al. | 560/125 |
| 4,193,936 | 3/1980 | Watson et al. | 424/324 |
| 4,248,859 | 2/1981 | Rowsell et al. | 424/324 |

OTHER PUBLICATIONS

Wagner et al., *Synthetic Organic Chemistry*, Wiley & Sons, N.Y., N.Y., 1955, pp. 571 & 647.
Singleton et al., JACS 60, pp. 540-543 (1938).

*Primary Examiner*—Thomas A. Waltz
*Attorney, Agent, or Firm*—Arthur I. Palmer, Jr.

[57] ABSTRACT

This invention provides an improved process for synthesizing carboxamides which involves reacting 3-p-menthyl halide with magnesium to form 3-p-menthylmagnesium halide Grignard reagent, and reacting the Grignard reagent with hydrocarbyl isocyanate at a temperature below about $-20°$ C. to form N-hydrocarbyl-p-menthane-3-carboxamide product.

The product comprises a mixture of geometric isomers in which the 3-p-menthyl:3-p-neomenthyl weight ratio is at least 4:1 and can be as high as 9:1 under optimal conditions.

This invention also provides a novel process for producing acylurea compounds such as N-(3-p-menthylcarbonyl)-N-t-butyl-N'-t-butylurea.

20 Claims, No Drawings

PROCESS FOR SYNTHESIS OF N-(HYDROCARBYL)SUBSTITUTED-P-MENTHANE-3-CARBOXAMIDE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; and the like. The tobacco flavorants include compounds such as succinic anhydride; dihydroxyacetone; substituted pyridines; cinnamic derivatives; isovaleric acid; 6-methylhepta-3,5-dien-2-one; 2-butyl-2-butenal; 1,3-cyclohexadiene; alpha-pyrones; substituted butyrolactones; pyrazines and thiazolidines; and the like.

Cooling compounds, particularly methanol, have been used extensively in tobacco products. Unfortunately methanol has a high degree of volatility and also suffers from the disadvantage that it exhibits a relatively strong minty odor. Nevertheless, in spite of its disadvantages methanol is still extensively employed as a tobacco flavorant for the reason it has a physiological cooling effect on the mucous membranes of the mouth. Methanol flavorant in cigarette tobacco produces a cool sensation in the mouth during the smoking of a cigarette.

Other organic compounds are known which exhibit to some degree the properties of a physiological coolant. For example, N,N-dimethyl-2-ethylbutanamide is reported in French Pat. No. 1,572,332 as having a minty odor and a refreshing effect on mucous membranes. Other compounds of similar interest are 2,4,6-trimethylheptan-4-ol and 2,4,6-trimethylhept-2-en-4-ol as reported in Parfums-Cosmetiques-Savons, pages 17–20, May 1956.

More recently another group of organic compounds have been developed which are odorless and non-volatile, and which can function as physiologically active coolants. These compounds are the subject matter of the U.S. Pat. Nos. 4,178,459 and 4,193,936, and are generically classified as N-substituted para-methane carboxamides. Illustrative of a particularly interesting species as a prospective smoking tobacco flavorant is N-t-butyl-p-menthane-3-carboxamide:

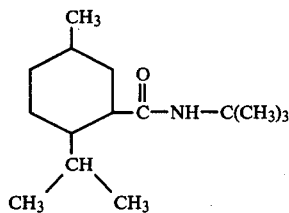

The said patents describe a sequence of conventional reactions for producing the N-substituted para-menthane carboxamides. Thus, N-t-butyl-p-menthane-3-carboxamide is produced by the following sequence of reactions:

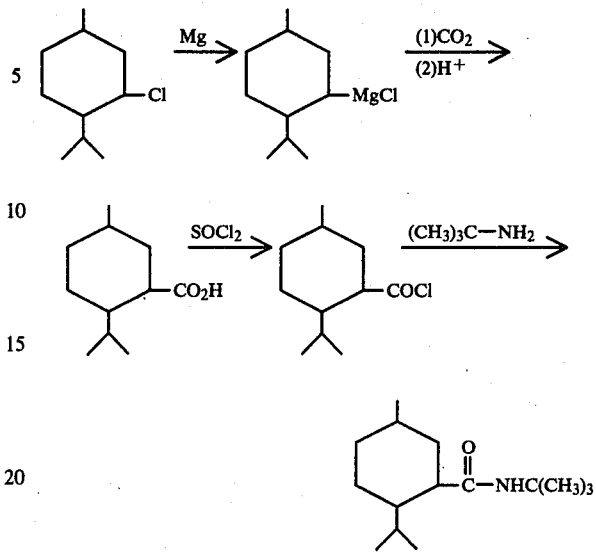

The reaction sequence is long and tedious, and the overall conversion from 3-p-methyl halide to N-t-butyl-p-menthane-3-carboxamide is inefficient.

In copending patent application Ser. No. 258,207, filed Apr. 27, 1981, there is described a novel process for producing N-(hydrocarbyl)substituted-p-menthane-3-carboxamide compounds in general, and N-t-butyl-p-menthane-3-carboxamide in particular. The said novel process in a preferred embodiment comprises (1) reacting 3-p-methyl halide with magnesium in an anhydrous solvent medium to form 3-p-methylmagnesium halide; and (2) reacting the 3-p-methylmagnesium halide with t-butyl isocyanate to form N-t-butyl-p-menthane-3-carboxamide product.

A noteworthy aspect of the said novel process is that the N-t-butyl-p-menthane-3-carboxamide product is a mixture of 3-p-menthyl and 3-p-neomenthyl geometric isomers. When step (2) of the process is conducted at a temperature between about 0°–30° C., the quantity of the 3-p-menthyl isomer present in the isomer product mixture varies in the range between about 57–80 weight percent, based on the combined weight of the 3-p-menthyl and 3-p-neomenthyl isomers.

The relative ratio of 3-p-menthyl to 3-p-neomenthyl isomers in the final product is generally felt to be a significant factor when the physiological coolant properties of the said isomeric mixture is of primary importance.

It is well known that the p-menthane structure can exist in cis and trans forms. Substitution of a group (e.g., carboxamide) into the 3-position gives rise to four geometric isomers, depending upon whether the substituted group in the 3-position is an axial or equatorial configuration in each of the cis or trans isomers. The four geometric isomers are related as menthol is to neomenthol, isomenthol and neoisomenthol.

In general, it is found that among p-menthane-3-carboxamide compounds the equatorial 3-carboxamide derivatives (i.e., a 3-p-menthyl configuration) have a greater physiological coolant effect than do the axial 3-carboxamide derivatives (i.e., a 3-p-neomenthyl configuration). Since they have superior physiological coolant properties, p-menthane-3-carboxamide isomers are much preferred over p-neomenthane-3-carboxamide isomers for applications such as tobacco flavorants.

Accordingly, it is a main object of this invention to provide an improved process for producing N-(hydrocarbyl)substituted-p-methane-3-carboxamide compounds.

It is a further object of this invention to provide an improved process for converting 3-p-menthyl halide to N-(hydrocarbyl)substituted-p-menthane-3-carboxamide, wherein the 3-carboxamide product comprises a mixture of 3-p-menthyl and 3-p-neomenthyl isomers in which the content of 3-p-menthyl isomer is at least about 90 weight percent, and the content of 3-p-neomenthyl isomer is less than about 10 weight percent.

Other objects and advantages of the present invention will become apparent from the accompanying description and examples.

DESCRIPTION OF THE INVENTION

One or more objects of the present invention are accomplished by the provision of a process for the synthesis of N-hydrocarbyl-p-menthane-3-carboxamide which comprises (1) reacting 3-p-menthyl halide with magnesium in an anhydrous solvent medium to form 3-p-menthylmagnesium halide; and (2) reacting the 3-p-menthylmagnesium halide with hydrocarbyl isocyanate at a temperature below about −20° C. to form N-hydrocarbyl-p-menthane-3-carboxamide product. The process is illustrated by the following reaction sequence for the production of N-t-butyl-p-menthane-3-carboxamide:

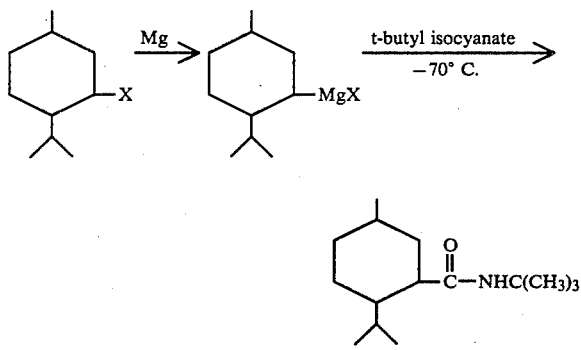

The 3-p-menthyl halide reactant in step(1) preferably is selected from 3-p-menthyl chloride and 3-p-menthyl bromide.

The step(1) procedure is accomplished in accordance with conventional Grignard reagent preparation techniques. In a typical case, the step(1) reaction is conducted in a nonreactive solvent medium (e.g., benzene, diethyl ether or tetrahydrofuran) with the rigorous exclusion of moisture.

The step(1) reaction temperature will vary in the range between about 0° and 100° C., and normally will be in the range between about 20°–75° C.

The solvent solution of 3-p-menthylmagnesium halide Grignard reagent obtained as a product of the step(1) procedure is in a convenient form for direct use in step(2) of the process. The quantity of Grignard reagent prepared in step(1) can be calculated to satisfy the prospective stoichiometry of the step(2) reaction.

The 3-p-menthylmagnesium halide and hydrocarbyl isocyanate reactants in step(2) are employed in an approximately equimolar ratio, i.e., a halide:isocyanate ratio between about 0.7–1.5:1. The equimolar ratio facilitates product recovery and enhances the overall efficiency of the step(2) reaction.

It is an essential feature of the invention process that the step(2) reaction is conducted at a temperature below about −20° C., e.g., in the range between about −20° C. and −70° C. The slow rate of the reaction usually requires an average reaction period between about 20–80 hours. The reaction medium can be sampled and analyzed to monitor the progress of the step(2) reaction course toward completion.

The term "hydrocarbyl" as employed herein is meant to include acyclic and cyclic organic radicals containing between one and about 25 carbon atoms. The hydrocarbyl radical can contain heteroatoms (e.g., oxygen, nitrogen, sulfur and halogen) which do not interfere with the step(2) reaction between the Grignard reagent and the reactive isocyanate group of the hydrocarbyl isocyanate reactant.

It is preferred to exclude from the step(2) reaction medium the presence of any chemical functionality which is reactive with the isocyanate group. Particularly disadvantageous are groups containing active hydrogen sites, such as hydroxy, carboxy and amino groups.

Illustrative of hydrocarbyl radicals containing between about 1–25 carbon atoms are aliphatic, alicyclic and aromatic radicals such as methyl, ethyl, propyl, butyl, isobutyl, 2-ethylhexyl, decyl, butenyl, hexenyl, cyclopropyl, cyclopentyl, cyclopentenyl, cyclohexyl, cyclohexenyl, ethoxyethyl, acetylethyl, acetoxyethyl, methoxypropyl, methylthiocyclohexyl, phenyl, tolyl, methoxyphenyl, fluorophenyl, benzyl, phenylethyl, naphthyl, pyridyl, pyrazyl, furyl, thiazyl, thienyl, and the like.

The hydrocarbyl isocyanate compounds can be prepared by conventional synthesis methods, such as by the reaction of the corresponding hydrocarbyl primary amine compound with phosgene.

One important advantage of the invention process is the high yield conversion which is achieved in the step(2) interaction of 3-p-menthylmagnesium halide with hydrocarbyl isocyanate. Thus, unexpectedly the relative conversion efficiency of the reaction between 3-p-menthylmagnesium halide and hydrocarbyl isocyanate at a given temperature is severalfold greater than the relative conversion efficiency of the reaction between 3-p-menthylmagnesium halide and carbon dioxide. It is to be noted that the latter carboxylation reaction is an intermediate step in the synthesis sequence illustrated above in connection with U.S. Pat. Nos. 4,178,459 and 4,193,936 in which the production of N-substituted para-menthane carboxamides is disclosed.

Another important advantage of the invention process is the selective high yield of 3-p-menthyl isomer (i.e., equatorial) in comparison with the yield of the less desirable 3-p-neomenthyl isomer (i.e., axial) which is obtained in step(2) of the process. Unexpectedly it was found that at a temperature below about −20° C., and preferably at a temperature in the range between about −30° C. and −70° C., at least 90 weight percent of 3-p-menthyl isomer is obtained from the step(2) reaction, as calculated on the basis of the combined weight of the 3-p-menthyl and 3-p-neomenthyl isomers. As demonstrated in Example II, as the reaction medium temperature increases in step(2) of the process the relative yield of 3-p-menthyl isomer in the product decreases, and the yield of 3-p-neomenthyl isomer increases.

A further advantage of the invention process is that it can be modified to produce a high yield of a novel species of acylurea product:

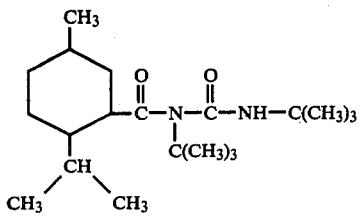

As demonstrated in Example III, the reaction of 3-p-menthylmagnesium halide with hydrocarbyl isocyanate at a temperature below about 0° C. produces a significant yield of the acylurea product illustrated above, i.e., N-(3-p-menthylcarbonyl)-N-t-butyl-N'-t-butylurea. As the temperature of the reaction medium is reduced, the yield of acylurea product increases.

The production of acylurea product is also favored if at least a stoichiometric quantity of hydrocarbyl reactant is employed, i.e., if two or more moles of hydrocarbyl isocyanate per mole of hydrocarbylmagnesium halide reactant (e.g., 2-10:1) are employed.

Another means of increasing the yield of acylurea product is by the slow addition of the hydrocarbyl Mg halide reactant to a reaction medium which contains a large molar excess of hydrocarbyl isocyanate reactant.

Thus, in another of its embodiments the present invention provides a process for producing acylurea compounds which comprises interacting hydrocarbylmagnesium halide with hydrocarbyl isocyanate in an anhydrous solvent medium at a temperature below about 0° C.:

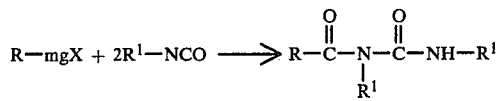

R and $R^1$ can be any hydrocarbyl substituent which does not contain any elements or functionality which might interfere with the Grignard reagent and isocyanate interaction in any substantial manner. The term "Hydrocarbyl" is as previously defined hereinabove. The term "halide" or the designation "X" refers to chloride, bromide or iodide elements.

It is preferred that the hydrocarbylmagnesium halide and hydrocarbyl isocyanate have solubility characteristics which permit their dissolution in a common solvent medium such as tetrahydrofuran.

A further embodiment of the present invention is based on the discovery that acylurea compounds of the type described above can be treated under alkaline conditions to yield carboxamide and carbamate products. As demonstrated in Example IV, the conversion of an acylurea under alkaline conditions proceeds as follows:

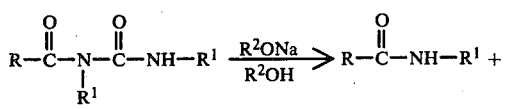

-continued $$R^2O-\overset{O}{\underset{\|}{C}}-NH-R^1$$

With reference to the synthesis of N-(hydrocarbyl)-substituted-p-menthane-3-carboxamide compounds, as a further embodiment this invention provides a process for the synthesis of N-hydrocarbyl-p-menthane-3-carboxamide which comprises (1) reacting 3-p-menthyl halide with magnesium in an anhydrous solvent medium to form 3-p-menthylmagnesium halide; (2) reacting the 3-p-menthylmagnesium halide with hydrocarbyl isocyanate at a temperature below about −20° C. to form N-hydrocarbyl-p-menthane-3-carboxamide and N-(3-p-menthylcarbonyl)-N-hydrocarbyl-N'-hydrocarbylurea; and (3) heating the N-(3-p-menthylcarbonyl)-N-hydrocarbyl-N'-hydrocarbylurea in a solvent medium under alkaline conditions to produce additional N-hydrocarbyl-p-menthane-3-carboxamide product.

The step(3) conversion reaction can be accomplished by treating the crude reaction product recovered from step(2), or alternatively the N-hydrocarbyl-p-menthane-3-carboxamide product can be separated from the crude reaction product before the crude product is subjected to heat treatment under the step(3) alkaline conditions.

Typically the step(3) procedure will be conducted in a solvent medium at a pH between about 7.5-12 and a temperature between about 30°-150° C. for a period between about 0.5-30 hours.

The solvent medium can be selected from ethers and alcohols such as tetrahydrofuran and methanol, or generally from any aqueous solutions of water-miscible solvents.

The step(3) alkalinity can be provided by any conventional basic reagent such as alkali metal hydroxides and alkoxides, and the like.

The following examples are further illustrative of the present invention. The reactants and other specific ingredients are presented as being typical, and various modifications can be derived in view of the foregoing disclosure within the scope of the invention.

EXAMPLE I

This Example illustrates the preparation of N-t-butyl-p-menthane-3-carboxamide in accordance with the present invention process.

A

Magnesium turnings (1.3 grams, 52 mmoles) were crushed in a mortar and placed in a 500 milliliter three-neck round bottom flask equipped with a magnetic stir bar, thermometer, addition funnel, condenser and nitrogen inlet. The apparatus was flame-dried and allowed to cool under a nitrogen atmosphere.

A crystal of iodine and about 5 milliliters anhydrous tetrahydrofuran were added to the reactor. The mixture was heated to reflux temperature, and 10 milliliters of a solution of freshly distilled 3-p-menthyl chloride (8.2 grams, 47 mmoles) in anhydrous tetrahydrofuran (25 milliliters) was added. The reaction started after several minutes, and the remainder of the 3-p-menthyl chloride solution was added dropwise over a period of 30-45 minutes. Some external heating was required to maintain reflux. On completion of this addition, the reaction mixture was refluxed an additional hour.

B

Half of the mixture as prepared above (about 23 mmoles) was transferred via syringe to a dry 250 milliliter three-neck round-bottom flask equipped with a magnetic stirring bar, rubber septum, nitrogen inlet and an addition funnel. The solution was cooled in dry ice-/acetone bath to $\leq -70°$ C.

With stirring, a solution of freshly distilled t-butyl isocyanate (2.4 grams, 24 mmoles) in anhydrous tetrahydrofuran (12.5 milliliters) was slowly added while maintaining the temperature at or below $-70°$ C. When addition was complete, the reaction mixture was stirred at $\leq -70°$ C. for 72 hours. The reaction was quenched by the slow addition of a mixture of methanol (10 milliliters) and tetrahydrofuran (15 milliliters). When addition of the quench solution was complete, the reaction was allowed to warm slowly to room temperature.

The mixture was dissolved in 200 milliliters of ether and extracted with 6 N hydrochloric acid, saturated sodium bicarbonate, 10% sodium thiosulfate, and brine. After the extraction procedures, the ether solution was dried over magnesium sulfate and then the solvent was evaporated. The recovered crude oil product was redissolved in hexane and evaporated several times to remove ether traces. Final evaporation yielded 4.59 grams of crude product.

High pressure liquid chromatography ($\mu$Porasil, 10% ethyl acetate/hexane) indicated that the material was a mixture of several components. The weight ratio of 3-p-menthyl:3-p-neomenthyl isomers was greater than 9:1. The separation of pure N-t-butyl-p-menthane-3-carboxamide was readily achieved by means of the liquid chromatography procedure.

EXAMPLE II

This Example illustrates the effect of temperature on the weight ratio of 3-p-menthyl and 3-p-neomenthyl isomers in the product recovered from step(2) of the invention process.

In a manner similar to that described in Example I, N-t-butyl-p-menthane-3-carboxamide was produced in three separate runs. The reactant proportions and reaction conditions were identical in each run, except that the reaction temperature was varied.

The results of the runs were as follows:

| Temperature | Yield[1] | Ratio[2] |
| --- | --- | --- |
| $-70°$ C. | approx. 24.2 | 90 |
| 0° C. | approx. 82.3 | 75 |
| 67° C. | approx. 87.4 | 60 |

[1]Weight percent of combined 3-p-menthyl and 3-p-neomenthyl isomers, based on the weight of 3-p-menthyl Mg chloride starting material consumed in step(1) of the process.
[2]Weight percent of 3-p-menthyl isomer, based on combined weight of 3-p-menthyl and 3-p-neomenthyl isomers.

The same temperature effect on isomer ratio is observed when the step(2) reaction is between 3-p-menthylmagnesium chloride or 3-p-menthylmagnesium bromide and isobutyl isocyanate, cyclopentyl isocyanate, phenyl isocyanate, tolylethyl isocyanate, naphthyl isocyanate, pyridyl isocyanate, pyrazyl isocyanate or pyrazylmethyl isocyanate.

EXAMPLE III

This Example illustrates the preparation of N-(3-p-menthylcarbonyl)-N-t-butyl-N'-t-butylurea, and the effect of temperature on product yield.

With the same materials and in a manner similar to that described in Example I, a series of runs were conducted at temperatures ranging from 67° C. to $-70°$ C. in step(2) of the process. The observed results are summarized in the Table.

The experimental data summarized in the Table indicated that the formation of acylurea product increased as the reaction temperature decreased.

As demonstrated in Example IV, the yield of N-t-butyl-p-menthane-3-carboxamide can be increased by heating the crude reaction product mixture obtained above under alkaline conditions. By means of the said heat treatment under alkaline conditions, N-(3-p-menthylcarbonyl-N-t-butyl-N'-t-butylurea is converted to N-t-butyl-p-menthane-3-carboxamide and a carbamate byproduct.

| Compound | Temperature | | | | | |
| --- | --- | --- | --- | --- | --- | --- |
| | +67° C. | +20° C. | 0° C. | −20° C. | −40° C. | −70° C. |
| %* I in all products | 60.7 | 75.6 | 76.9 | 75.8 | 40.7 | 21.6 |
| % II in all products | 26.7 | 9.8 | 5.4 | 3.5 | 3.3 | 2.6 |
| % Total I + II | 87.4 | 85.4 | 82.3 | 79.3 | 44.0 | 24.2 |
| % III in all products | 0 | 0 | 0 | 4.0 | 45.9 | 70.8 |
| % I + III in all products | 60.7 | 75.6 | 77.0 | 79.8 | 86.6 | 92.4 |

*The percentages are based on the weight of reacted grignard reagent.
Compound I is N—t-butyl-p-menthane-3-carboxamide.
Compound II is the neomenthyl isomer of Compound I.
Compound III is N—(3-p-menthylcarbonyl)-N—t-butyl-N'—t-butylurea.

EXAMPLE IV

This Example illustrates the conversion of N-(3-p-menthylcarbonyl)-N-t-butyl-N'-t-butylurea to N-t-butyl-p-menthane-3-carboxamide crude reaction product obtained in the manner of Example III was purified by liquid chromatography employing a RCM-100 column (Waters Associates, $\mu$-Porisil RCM 100-Module with silica cartridge).

A 52 milligram quantity of sodium was added to 5 milliliters of methanol. To this reaction medium was added a solution of 162 milligrams of purified N-(3-p-menthylcarbonyl)-N-t-butyl-N'-t-butylurea in about 7 milliliters of methanol.

The reaction mixture was refluxed for two hours, then cooled and evaporated to dryness under vacuum. The product residue was dissolved in ether, and the ether solution was washed with water and brine, then dried and evaporated under vacuum.

High pressure liquid chromatography indicated that the desired conversion was not complete. The product mixture was admixed with sodium methoxide (5.72 millimoles) and methanol (10 milliliters) and refluxed under a nitrogen atmosphere. The refluxing was continued (about 23 hours) until HPLC indicated that all the acylurea starting material had been converted to N-t-butyl-p-menthane-3-carboxamide. The identity of the carboxamide product was confirmed by NMR.

What is claimed is:

1. A process for the synthesis of N-hydrocarbyl-p-menthane-3-carboxamide which comprises (1) reacting 3-p-menthyl halide with magnesium in an anhydrous solvent medium to form 3-p-menthylmagnesium halide; and (2) reacting the 3-p-menthylmagnesium halide with hydrocarbyl isocyanate at a temperature between about $-30°$ C. and $-70°$ C. to form N-hydrocarbyl-p-menthane-3-carboxamide product.

2. A process in accordance with claim 1 wherein the 3-p-menthyl halide reactant in step(1) is 3-p-menthyl chloride.

3. A process in accordance with claim 1 wherein the 3-p-menthyl halide reactant in step(1) is 3-p-menthyl bromide.

4. A process in accordance with claim 1 wherein the 3-p-menthylmagnesium halide and hydrocarbyl isocyanate reactants in step(2) are employed in about an equimolar ratio.

5. A process in accordance with claim 1 wherein the hydrocarbyl isocyanate in step(2) is t-butyl isocyanate.

6. A process in accordance with claim 1 wherein the hydrocarbyl isocyanate in step(2) is 4-pyridyl isocyanate.

7. A process in accordance with claim 1 wherein the hydrocarbyl isocyanate in step(2) is pyrazylmethyl isocyanate.

8. A process in accordance with claim 1 wherein the step(2) reaction is conducted at a temperature at or below $-70°$ C.

9. A process in accordance with claim 1 wherein the step(2) reaction is conducted over a period between about 20-80 hours.

10. A process in accordance with claim 1 wherein the product of the process comprises a mixture of 3-p-menthyl and 3-p-neomenthyl isomers, and the quantity of 3-p-menthyl isomer in the product mixture is at least 90 weight percent, based on the combined weight of 3-p-menthyl and 3-p-neomenthyl isomers.

11. A process for the synthesis of N-hydrocarbyl-p-menthane-3-carboxamide which comprises (1) reacting 3-p-menthyl halide with magnesium in an anhydrous solvent medium to form 3-p-menthylmagnesium halide; (2) reacting the 3-p-menthylmagnesium halide with hydrocarbyl isocyanate at a temperature between about $-30°$ C. and $-70°$ C. to form a product mixture comprising N-hydrocarbyl-p-menthane-3-carboxamide and N-(3-p-menthylcarbonyl)-N-hydrocarbyl-N'-hydrocarbylurea; and (3) heating the N-(3-p-menthylcarbonyl)-N-hydrocarbyl-N'-hydrocarbylurea in a solvent medium under alkaline pH conditions to produce additional N-hydrocarbyl-p-menthane-3-carboxamide product.

12. A process in accordance with claim 11 wherein the 3-p-menthyl halide reactant in step(1) is 3-p-menthyl chloride.

13. A process in accordance with claim 11 wherein the 3-p-menthyl halide reactant in step(1) is 3-p-menthyl bromide.

14. A process in accordance with claim 11 wherein the 3-p-menthylmagnesium halide and hydrocarbyl isocyanate reactants in step(2) are employed in about an equimolar ratio.

15. A process in accordance with claim 11 wherein the hydrocarbyl isocyanate in step(2) is t-butyl isocyanate.

16. A process in accordance with claim 11 wherein the step(2) reaction is conducted at a temperature at or below $-70°$ C.

17. A process in accordance with claim 11 wherein the product mixture from step(2) is employed directly in step(3) without intermediate separation or purification of the product components.

18. A process in accordance with claim 11 wherein N-hydrocarbyl-p-menthane-3-carboxamide is removed from the step(2) product mixture before the said product mixture is subjected to the step(3) reaction conditions.

19. A process in accordance with claim 11 wherein the step(3) heating is conducted at a temperature in the range between about 30°-150° C.

20. A process in accordance with claim 11 wherein the step(3) alkaline pH is in the range between about 7.5-12.

* * * * *

UNITED STATES PATENT AND TRADEMARK OFFICE
CERTIFICATE OF CORRECTION

PATENT NO. : 4,366,317
DATED : December 28, 1982
INVENTOR(S) : Stephen A. Haut and Roger A. Comes It is certified that error appears in the above—identified patent and that said Letters Patent is hereby corrected as shown below:

Column 1, lines 22, 24, 27, and 30   Replace "methanol" by --menthol--.

Column 1, line 49   Replace "methane" by --menthane--.

Column 2, lines 25, 34, 35, and 36   Replace "-methyl" by --menthyl--.

Column 3, line 5   Replace "-methane-" by --menthane--.

Signed and Sealed this

Sixteenth Day of August 1983

[SEAL]

Attest:

Attesting Officer

GERALD J. MOSSINGHOFF

Commissioner of Patents and Trademarks